(12) United States Patent
Flanary (10) Patent No.: US 10,260,507 B2
(45) Date of Patent: Apr. 16, 2019

(54) MAGNETICALLY COUPLED PUMP ASSEMBLY

(75) Inventor: Ronald Flanary, Blacksburg, VA (US)

(73) Assignee: Moog Inc., East Aurora, NY (US)

( * ) Notice: Subject to any disclaimer, the term of this patent is extended or adjusted under 35 U.S.C. 154(b) by 503 days.

(21) Appl. No.: 13/593,337

(22) Filed: Aug. 23, 2012

(65) Prior Publication Data

US 2013/0129541 A1 May 23, 2013

Related U.S. Application Data (60) Provisional application No. 61/526,636, filed on Aug. 23, 2011.

(51) Int. Cl.
| | |
|---|---|
| *F04D 1/04* | (2006.01) |
| *F04D 7/02* | (2006.01) |
| *A61M 16/10* | (2006.01) |
| *A61M 16/16* | (2006.01) |
| *F04B 17/00* | (2006.01) |
| *F04D 13/02* | (2006.01) |

(Continued)

(52) U.S. Cl.
CPC ....... *F04D 13/027* (2013.01); *A61M 16/1075* (2013.01); *A61M 16/162* (2013.01); *F04B 17/00* (2013.01); *F04D 13/025* (2013.01); *F04D 13/064* (2013.01); *F04D 13/0626* (2013.01); *F04D 25/026* (2013.01); *F04D 25/0606* (2013.01); *A61M 16/109* (2014.02); *A61M 2202/0208* (2013.01); *A61M 2205/3331* (2013.01); *A61M 2205/3368* (2013.01); *A61M 2205/3389* (2013.01); *A61M 2205/3653* (2013.01); *F04D 1/04* (2013.01); *F04D 7/02* (2013.01); *F04D 29/2216* (2013.01); *F04D 29/2222* (2013.01)

(58) Field of Classification Search
CPC .............. F04D 1/04; F04D 7/02–7/045; F04D 13/024–13/027; F04D 13/06; F04D 13/0626–13/064; F04D 17/08; F04D 25/026; F04D 25/06; F04D 29/22; F04D 29/2216–29/2227; F04D 29/2288–29/2294; F04D 29/628; F04D 25/0606; F04D 17/00; A61M 16/1075; A61M 16/162; A61M 2205/3331; A61M 2205/3368; A61M 2205/3389; A61M 2205/3653
USPC ............ 417/420, 353, 356, 357, 366, 423.1, 417/423.7, 423.11, 423.14, 424.1, 424.2; 310/43, 156.01, 156.26, 264, 265

See application file for complete search history.

(56) References Cited

U.S. PATENT DOCUMENTS 3,238,878 A * 3/1966 Martin .......................... 417/370
3,354,833 A * 11/1967 Laing .................... F16C 25/045
310/104

(Continued)

*Primary Examiner* — Alexander B Comley
(74) *Attorney, Agent, or Firm* — Hodgson Russ LLP (57) ABSTRACT

Embodiments of the invention provide a pump assembly including a pump chamber with an inlet and an outlet. The pump assembly also includes a first cup at least partially enclosing the pump chamber and including a protrusion with a central recess, and a shaft positioned within the central recess. The pump assembly further includes a substantially hemispherical rotor unit with at least one ferrous metal element molded in plastic, and an impeller coupled to the rotor unit. The rotor unit and the impeller are positioned inside the first cup and rotatable around the shaft.

15 Claims, 8 Drawing Sheets

(51) Int. Cl.
*F04D 13/06* (2006.01)
*F04D 25/02* (2006.01)
*F04D 25/06* (2006.01)
*F04D 29/22* (2006.01)

(56) References Cited

U.S. PATENT DOCUMENTS

| | | | | |
|---|---|---|---|---|
| 3,490,379 | A | * | 1/1970 | Laing .................... F04D 13/024 251/249.5 |
| 4,047,847 | A | * | 9/1977 | Oikawa ........................ 417/370 |
| 4,080,112 | A | * | 3/1978 | Zimmermann ............... 417/420 |
| 4,115,040 | A | * | 9/1978 | Knorr .......................... 417/420 |
| 4,226,574 | A | * | 10/1980 | Villette ........................ 417/420 |
| 4,752,194 | A | * | 6/1988 | Wienen et al. ............... 417/420 |
| 4,834,628 | A | * | 5/1989 | Laing ........................... 417/420 |
| 4,854,823 | A | * | 8/1989 | Hatting et al. ................. 417/63 |
| 4,954,736 | A | * | 9/1990 | Kawamoto ............ H02K 1/278 310/156.21 |
| 4,998,863 | A | * | 3/1991 | Klaus .............................. 417/63 |
| 5,248,245 | A | * | 9/1993 | Behnke et al. ................ 417/366 |
| 5,464,333 | A | * | 11/1995 | Okada et al. ................. 417/420 |
| 5,779,456 | A | * | 7/1998 | Bowes .................. F04D 13/027 417/420 |
| 5,915,931 | A | * | 6/1999 | Lindner et al. ............... 417/420 |
| 6,135,728 | A | * | 10/2000 | Klein et al. ................... 417/420 |
| 6,293,772 | B1 | * | 9/2001 | Brown .................. F04D 29/041 415/122.1 |
| 6,443,710 | B1 | * | 9/2002 | Tatsukami et al. ............ 417/365 |
| 6,607,370 | B2 | * | 8/2003 | Fukamachi et al. .......... 417/420 |
| 7,249,939 | B2 | * | 7/2007 | Yanagihara et al. .......... 417/420 |
| 7,500,829 | B2 | * | 3/2009 | Edwards et al. ........... 416/170 R |
| 7,549,205 | B2 | * | 6/2009 | Shafer ............................. 29/446 |
| 7,707,720 | B2 | * | 5/2010 | Klein et al. .................. 29/888.024 |
| 2002/0054820 | A1 | * | 5/2002 | Fukamachi et al. .......... 417/420 |
| 2003/0152462 | A1 | * | 8/2003 | Yaegashi .................. A61M 1/101 417/42 |
| 2008/0240947 | A1 | * | 10/2008 | Allaire et al. ................. 417/420 |
| 2012/0156071 | A1 | | 6/2012 | Hijikata et al. |

* cited by examiner

MAGNETICALLY COUPLED PUMP ASSEMBLY

RELATED APPLICATIONS

This application claims priority under 35 U.S.C. § 119 to U.S. Provisional Patent Application No. 61/526,636 filed on Aug. 23, 2011, the entire contents of which is incorporated herein by reference.

BACKGROUND

Respiratory care products, such as those used to provide humid, temperature-controlled oxygen to patients, require a substantially sterile environment for transmitting the oxygen to a patient. In such products, a machine with a pump unit is used to pump water through a fluid circuit including a vapor transfer cartridge that mixes the water with breathing gases (including a specific oxygen percentage) so that the breathing gases being provided to the patient are at a desired humidity level.

In conventional machines, at least a portion of the pump unit is disposable so that the machine is reusable without contaminating the breathing gases supplied to a patient. For example, the pump unit includes a disposable cartridge which is disposed of after each patient use. The disposable cartridge includes rare earth magnets, which are activated by a magnet in the permanent portion (e.g., the capital unit or base unit) of the machine. Activation of the rare earth magnets can cause rotation of an impeller in the disposable cartridge to pump the water through the fluid circuit. While this allows separation between the water in the disposable cartridge and the reusable capital unit of the machine, the disposable cartridges are rather expensive due to the use of rare earth magnets.

SUMMARY

Some embodiments of the invention provide a pump assembly including a pump chamber with an inlet and an outlet. The pump assembly also includes a first cup at least partially enclosing the pump chamber and including a protrusion with a central recess, and a shaft positioned within the central recess. The pump assembly further includes a substantially hemispherical rotor unit with at least one ferrous metal element molded in plastic, and an impeller coupled to the rotor unit. The rotor unit and the impeller are positioned inside the first cup and rotatable around the shaft.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Some embodiments of the invention provide a magnetically coupled pump assembly with a permanent stator unit and a disposable portion containing an impeller and a rotor unit for rotating the impeller. The rotor unit can include ferrous metal elements, such as magnetic stainless steel, molded with a plastic to form a solid rotor cup, and a ring magnet in the stator unit can induce rotation of the ferrous metal elements. The use of ferrous metal elements like magnetic stainless steel, rather than conventional rare earth magnets, can greatly reduce the cost of the disposable cartridge.

Figure 1:
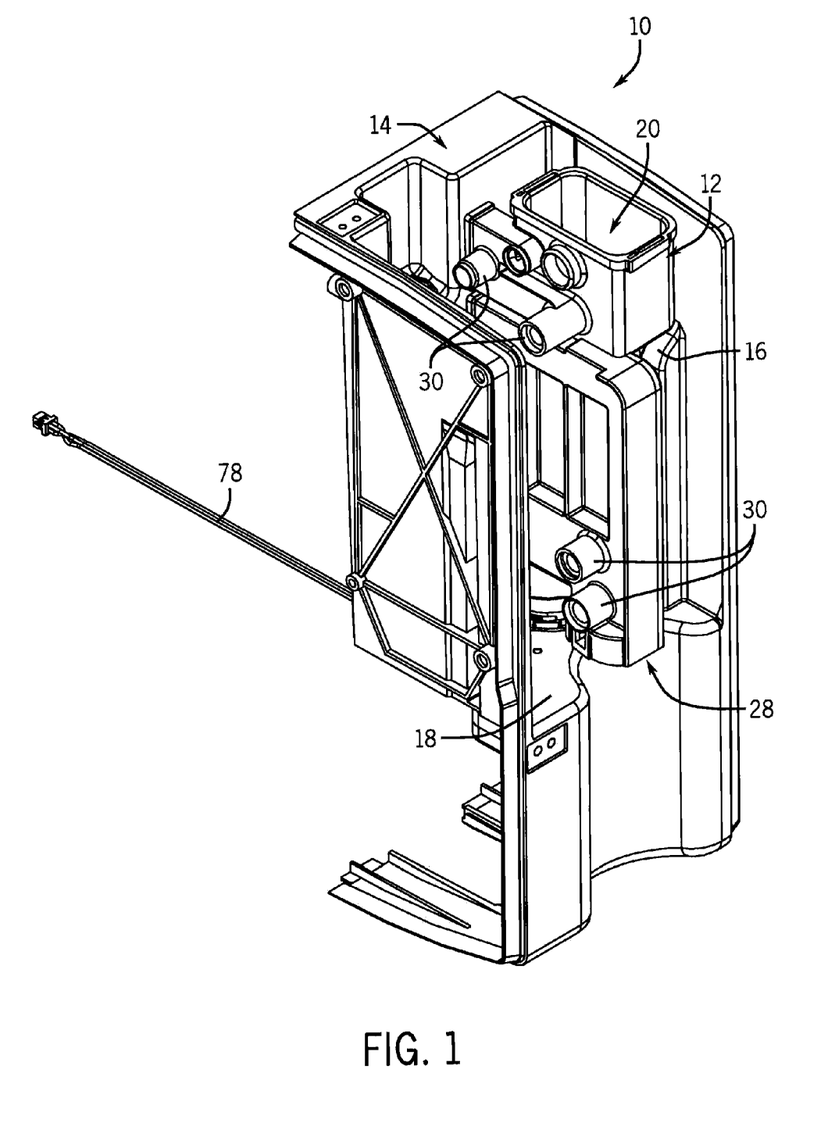
FIG. 1 is a partial front perspective view of a respiratory care system.
Figure 2:
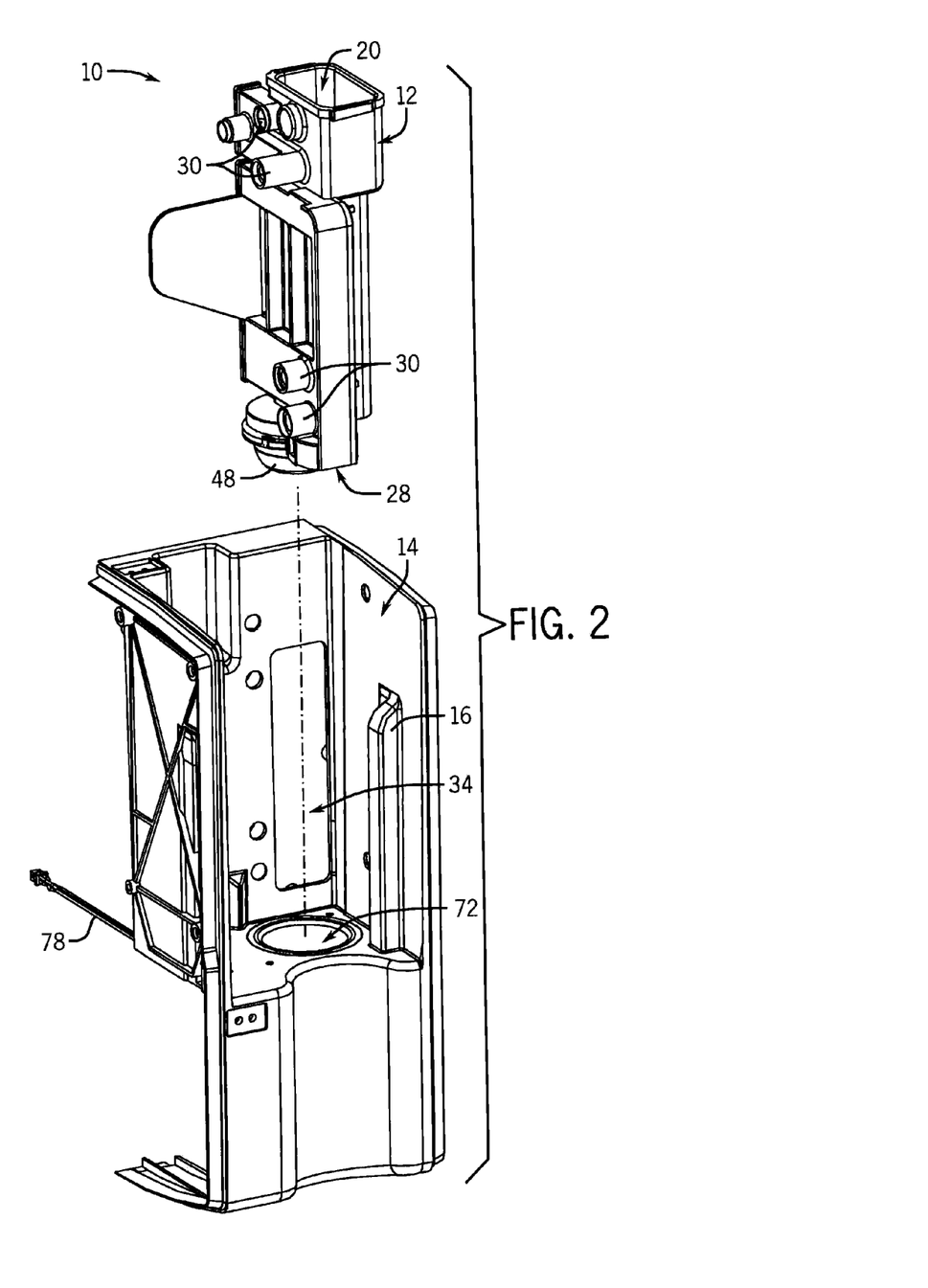
FIG. 2 is an exploded perspective view of the respiratory care system of FIG. 1.

FIG. 1 illustrates a portion of a respiratory care system 10 that delivers heated and humidified breathing gases to a patient. The respiratory care system 10 includes a disposable vapor transfer unit 12 and a reusable base unit 14. The vapor transfer unit 12 can be releasably engaged with the base unit 14. For example, as shown in FIG. 2, the vapor transfer unit 12 can be slid along a track 16 on the base unit 14 until the vapor transfer unit 12 is seated within the base unit 14 (e.g., on a seat portion 18 of the base unit 14) and/or until snap fit connections (not shown) between the base unit 14 and the vapor transfer unit 12 are engaged. The base unit 14 can also include a control section (not shown) for operating the respiratory care system 10.

Figure 3:
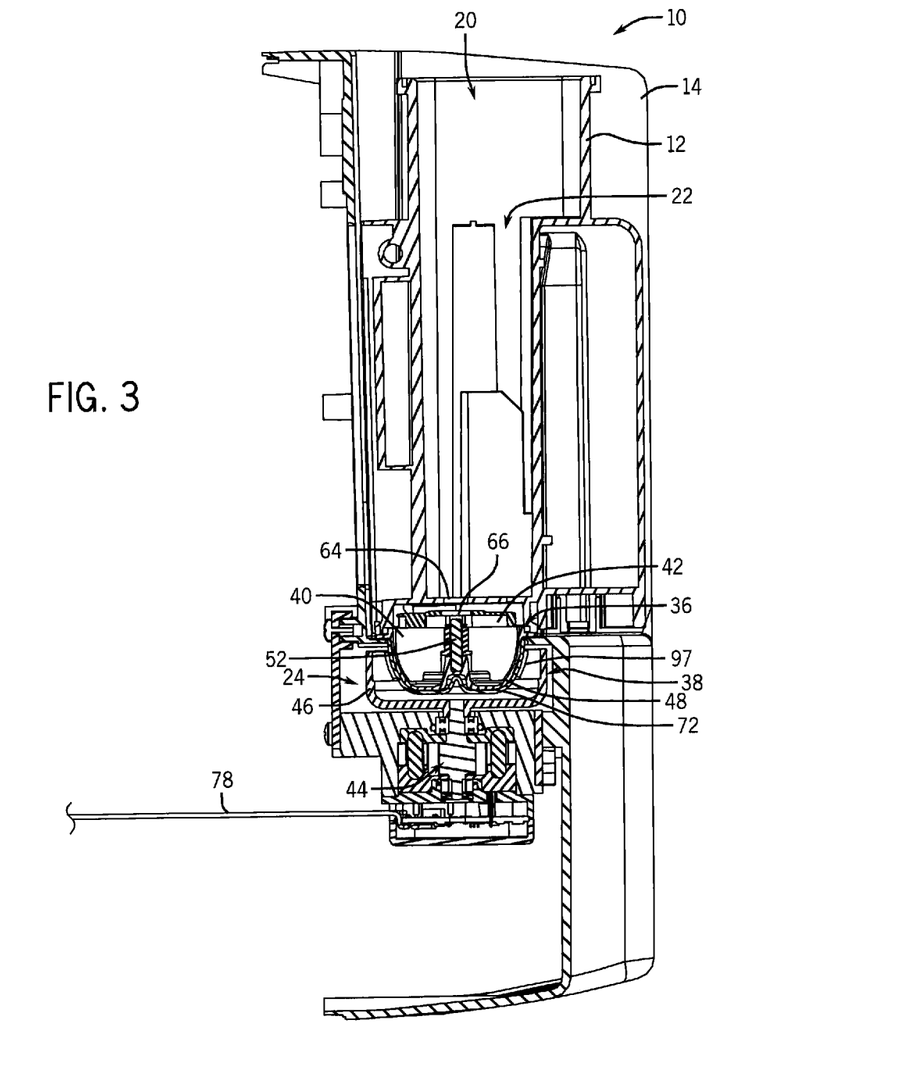
FIG. 3 is a cross-sectional view of the respiratory care system of FIG. 1.
Figure 4:
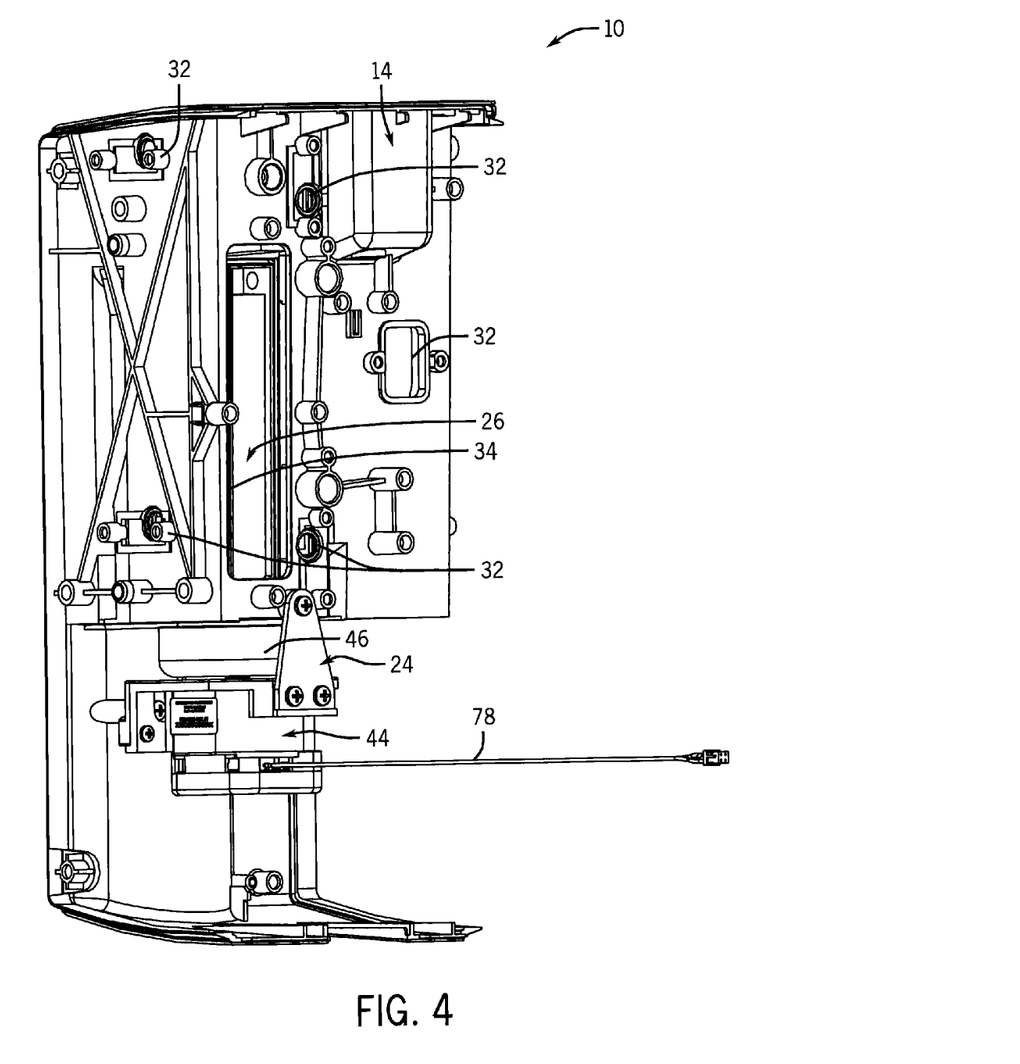
FIG. 4 is a rear perspective view of the respiratory care system of FIG. 1.
Figure 5:
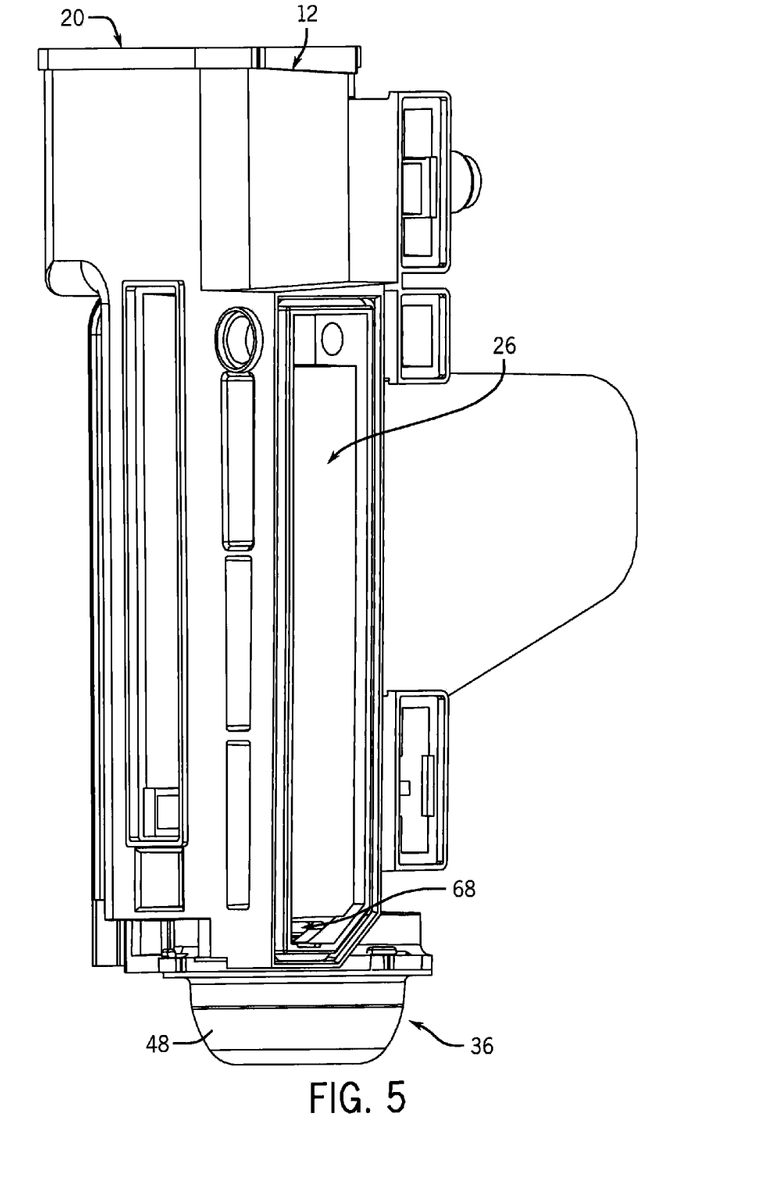
FIG. 5 is a rear perspective view of a vapor transfer unit for use with the respiratory care system of FIG. 1.

During operation, a liquid, such as water, is introduced into the vapor transfer unit 12 and pumped through a fluid circuit within the vapor transfer unit 12. Through the fluid circuit, the water is stored, heated, and mixed with breathing gases. The breathing gases, warmed and humidified by mixing with the heated water, are then supplied to a patient. More specifically, water can be introduced through a water inlet section 20 into a water reservoir 22, as shown in FIG. 3, for example from a water bag. The water reservoir 22 can be in fluid communication with a pump assembly 24, as further described below, that pumps water from the water reservoir 22 past a heating area 26, as shown in FIGS. 4 and 5, through a patient delivery tube (not shown), through a vapor transfer cartridge (not shown), and back into the water reservoir 22, completing the fluid circuit. Breathing gases, which can include a user-controlled percentage of oxygen or nitric oxide, are introduced from the base unit 14 into the vapor transfer unit 12, through the vapor transfer cartridge for humidification from the passing water, and through the patient delivery tube to the patient. The water circulating through the patient delivery tube can maintain the temperature of the breathing gases as they are supplied to the patient and can minimize condensation. The patient delivery tube can be coupled to the vapor transfer unit 12 at patient delivery tube connections 28 and the vapor transfer cartridge can be coupled to the vapor transfer unit 12 at cartridge connections 30, as shown in FIGS. 1 and 2. The vapor transfer unit 12 and the base unit 14 can also include multiple aligned sensor interfaces 32 to monitor the fluid circuit, as shown in FIG. 4. For example, optical sensors (e.g., part of the control section) can detect the level of water within the reservoir 22 and temperature sensors can detect the temperature of water traveling from the heating area 26 toward the patient delivery tube and from the patient delivery tube toward the vapor transfer cartridge. In addition, the base unit 14 can include a heater interface 34, as shown in FIG. 4, that aligns with the heating area 26 of the vapor transfer unit 12 so that a heat plate (not shown) of the control section can heat water flowing through the heating area 26.

As described above, the pump assembly 24 can pump water through the fluid circuit. The pump assembly 24 can be split into a first portion 36 (i.e., a disposable portion) that is part of the vapor transfer unit 12 and a second portion 38 (i.e., a reusable portion) that is part of the base unit 14. The first portion 36, which is in contact with water of the fluid circuit, includes a rotor unit 40 with an impeller 42. The second portion 38, which remains dry and does not contact water of the fluid circuit, includes a motor 44 and a stator unit 46. The first portion 36 and the second portion 38 can be removably coupled together so that the first portion 36 can be disposed of with the vapor transfer unit 12 after each patient use, while the second portion 38 can remain in the base unit 14 for reuse without the risk of contamination from the fluid circuit. As a result, the pump assembly 24 arranged in this manner with a disposable portion 36 and a reusable portion 38 can be used in the respiratory care system 10 or other sterile applications that require a disposable pumping section for multiple patient uses, such as continuous positive airway pressure (CPAP) machines. In addition, the pump assembly 24 can be used in non-medical applications that require a rotor unit physically separable from, or removably coupled to, a stator unit.

Figure 6:
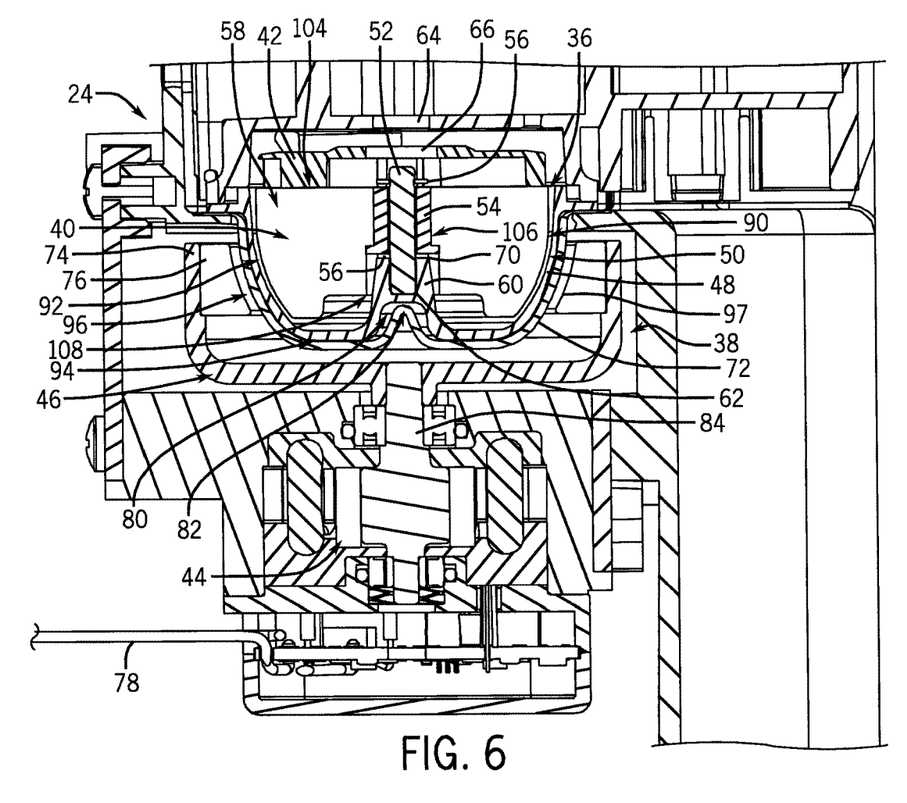
FIG. 6 is another cross-sectional view of the respiratory care system of FIG. 1.

As shown in FIGS. 3 and 6, the first portion 36 can include a first cup 48 with a curved inner surface 50, a stationary shaft 52, a main bearing 54, and secondary bearings 56. The first cup 48 encloses the rotor unit 40 and the impeller 42 within a pump chamber 58 of the vapor transfer unit 12 and can include a protrusion 60 with a central recess 62. The stationary shaft 52 can be set within the central recess 62 and the bearings 54, 56 can be positioned around the stationary shaft 52. During operation, the rotor unit 40, the impeller 42, and the bearings 54, 56 can rotate around the stationary shaft 52. More specifically, the impeller 42 can be coupled to the rotor unit 40 so that rotation of the rotor unit 40 (driven by the stator unit 46, as described below) causes rotation of the impeller 42 to pump water within the pump chamber 58. In this manner, the pump assembly 24 acts as a centrifugal pump by receiving water (e.g., from the water reservoir 22) axially from a pump chamber inlet 64 through an eye 66 of the impeller 42, and outputting pressurized water radially from the impeller 42 toward a pump chamber outlet 68 (e.g., toward the heating area 26, as shown in FIG. 5). In addition, water from the water reservoir 22 can substantially flood the entire pump chamber 58, causing the rotor unit 40 to float within the first cup 48. The stationary shaft 52 resting within the central recess 62 of the first cup 48, and the bearings 54, 56 resting on an annular shoulder 70 of the protrusion 60, can help keep the rotor unit 40 centered within the first cup 48.

In some embodiments, the second portion 38 can include a second cup 72, the stator unit 46 with a stator cup 74 and a ring magnet 76, and the motor 44 with electrical connections 78. The second cup 72 can substantially enclose the stator unit 46 (i.e., from the seat portion 18 of the base unit 14). As a result, during engagement of the vapor transfer unit 12 and the base unit 14, the first cup 48 can sit within the second cup 72. Also, in some embodiments, as shown in FIGS. 3 and 6, the first cup 48 and the second cup 72 can include a mating recess 80 and protrusion 82, respectively, to aid in aligning the first cup 48 within the second cup 72 during engagement of the vapor transfer unit 12 and the base unit 14. The first cup 48 and the second cup 72 can ensure sterility of the pump assembly 24 by physically separating the rotor unit 40 and the stator unit 46 and preventing contamination of the reusable stator unit 46 with water from the fluid circuit.

Figure 7:
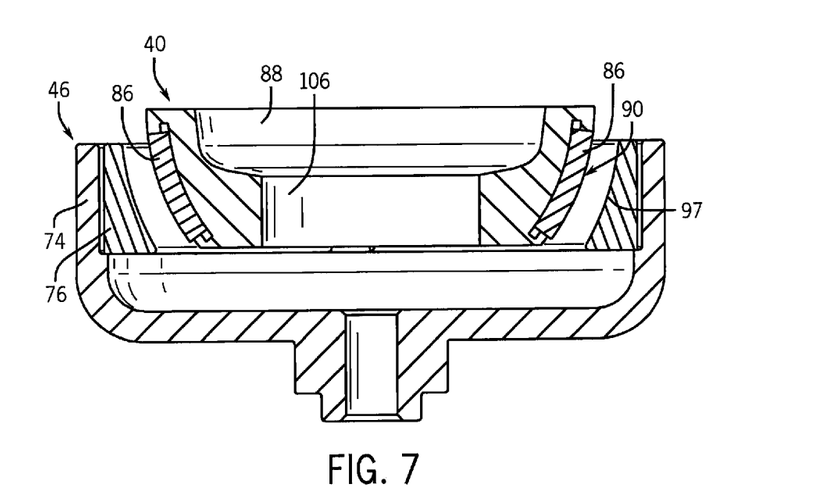
FIG. 7 is a cross-sectional view of a stator unit and a rotor unit, according to one embodiment of the invention, for use with the respiratory care system of FIG. 1.
Figure 8:
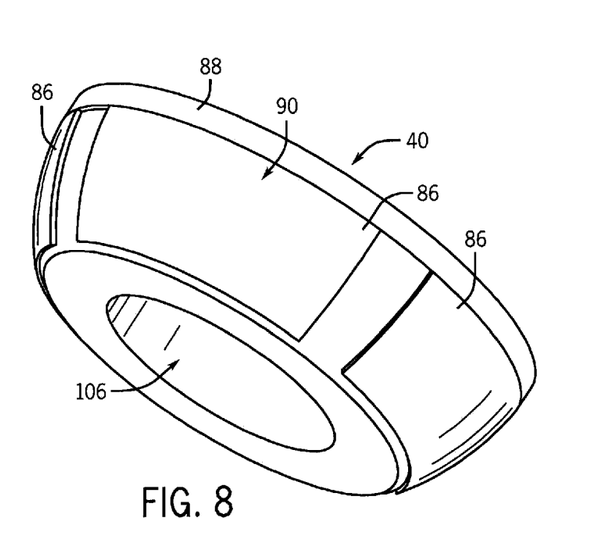
FIG. 8 is a perspective view of the rotor unit of FIG. 7.

In addition, with respect to the stator unit 46, the stator cup 74 can be coupled to a motor shaft 84 of the motor 44 and the ring magnet 76 can be positioned within the stator cup 74 so that it encircles the rotor unit 40 when the vapor transfer unit 12 is engaged with the base unit 14. As shown in FIGS. 7 and 8, the rotor unit 40 can include one or more ferrous metal elements 86, causing a magnetic coupling between the rotor unit 40 and the ring magnet 76 of the stator unit 46. As a result, the motor 44 can drive the stator cup 74 and the ring magnet 76 through rotation of the motor shaft 84, which in turn can drive the rotor unit 40 and cause rotation of the impeller 42 to pump water through the fluid circuit.

As described above, the rotor unit 40 can include multiple ferrous metal elements 86, such as magnetic stainless steel elements. The ferrous metal elements 86 can be substantially curved and can be transfer molded using a plastic 88, such as epoxy, to form a solid, substantially hemispherical shape with the ferrous metal elements 86 positioned around its outside. In some embodiments, the rotor unit 40 can include four ferrous metal elements 86. The use of the ferrous metal elements 86 in the disposable vapor transfer unit 12 can substantially reduce the cost of the pump assembly 24, in comparison to conventional assemblies that use rare earth magnets. In addition, the use of the transfer molded epoxy 88 within the rotor unit 40 can substantially reduce the cost of the pump assembly 24 in comparison to conventional assemblies with solid metal rotor units.

The hemispherical shape of the rotor unit 40 can provide a curved outer surface 90 that allows a substantially close fit of the rotor unit 40 within the first cup 48 (e.g., matching the curved inner surface 50 of the first cup 48) to minimize a water gap 92 between the rotor unit 40 and the first cup 48, which can improve the strength of the magnetic coupling between the ferrous metal elements 86 and the ring magnet 76 of the stator unit 46 (which also must be coupled over a first air gap 94 formed between the first cup 48 and the second cup 72, as well as a second air gap 96 between the ring magnet 76 and the second cup 72). In addition, the curved outer surface 90 can provide more surface area, in comparison to a slanted or straight outer surface, resulting in a greater magnetic coupling between the ferrous metal elements 86 and the ring magnet 76. The curved outer surface 90 can therefore allow coupling of a necessary amount of torque required for the rotor unit 40 and the impeller 42 to sufficiently pump the water in the fluid circuit, despite the physical separation and varying water and air gaps 92, 94, 96 between the rotor unit 40 and the stator unit 46 (e.g., due to rotor unit tilt). In addition, as shown in FIGS. 3, 6, and 7, the ring magnet 76 can include a curved inner surface 97 that substantially mimics the curved outer surface 90 of the rotor unit 40. The curved inner surface 97 can further strengthen the magnetic coupling, for example by minimizing the air gap 96 and providing additional magnetic surface area, in comparison to traditional straight ring magnets or a series of bar magnets.

Figure 9:
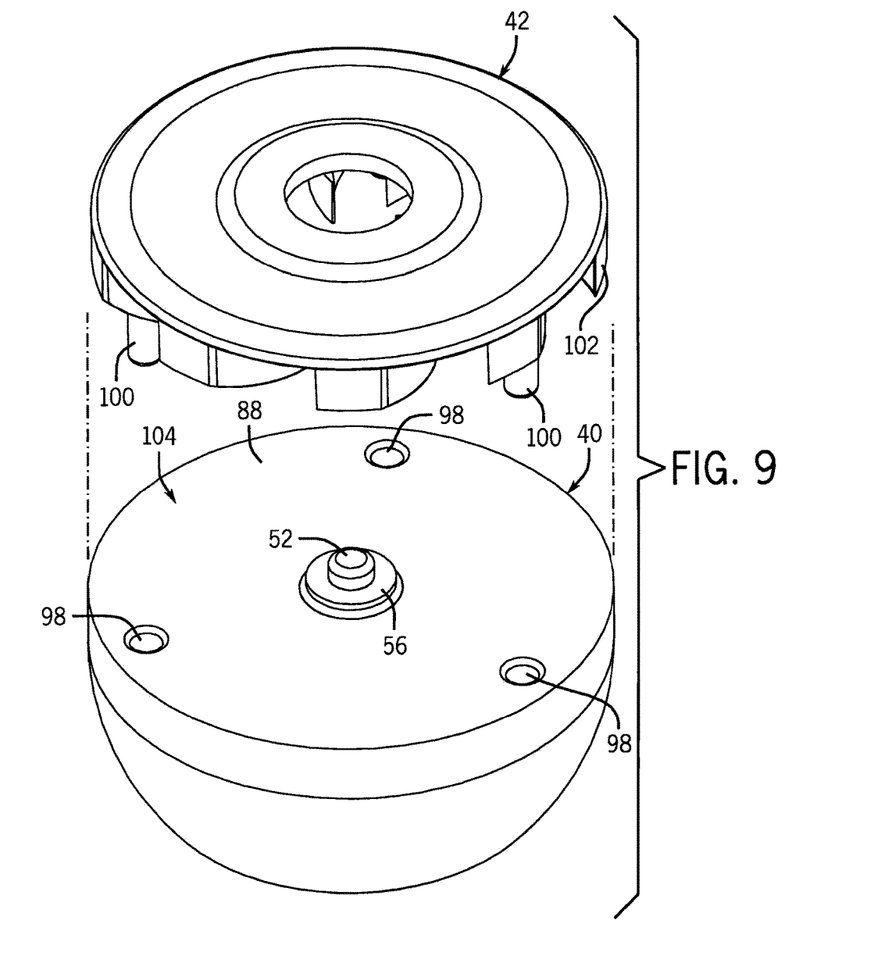
FIG. 9 is a partial exploded view of a rotor unit and an impeller, according to one embodiment of the invention, for use with the respiratory care system of FIG. 1.

In some embodiments, the rotor unit 40 can include receiving holes 98 that can receive protrusions 100 of the impeller 42 in order to couple the impeller 42 and the rotor unit 40 together, as shown in FIG. 9. The protrusions 100 can extend past impeller vanes 102 so that, when the impeller 42 and the rotor unit 40 are coupled together, the impeller vanes 102 can rest on or just above an upper surface 104 of the rotor unit 40. In addition, as shown in FIG. 6, the rotor unit 40 can include a central cutout 106 through the epoxy 88. An upper portion of the central cutout 106 can include a diameter or diameters substantially equal to the outer diameter or diameters of the main bearing 54. The rotor unit 40 can be press-fit, over-molded, or glued to the main bearing 54. A lower portion of the central cutout 106 can include a second diameter larger than the diameters of the upper portion, creating an annular shoulder 108.

As described above, the curved outer surface 90 of the rotor unit 40 can help minimize the water gap 92 and can increase the surface area for magnetic coupling. The curved outer surface 90 can also help counteract both axial and radial forces to maintain the rotor unit 40 in a substantially centered position within the first cup 48. For example, the rotor unit 40 and the impeller 42 can be positioned over the shaft 52 until the main bearing 54 is seated on the protrusion 60, and motion of the rotor unit 40 and the impeller 42 is restricted by the components enclosing the pump chamber 58, such as the first cup 48. The rotor unit 40 and the impeller 42 may not touch these components when magnetically coupled to the stator unit 46 because the coupling pulls the rotor unit 40 down axially along the shaft 52. Furthermore, the annular shoulder 108 can assist with centering the rotor unit 40 by preventing the rotor unit 40 from excessively tipping axially. More specifically, the annular shoulder 108 will contact the protrusion 60 of the first cup 48 if the rotor unit 40 begins to tip axially, therefore preventing the rotor unit 10 from excessive tipping. In addition, the central cutout 106 can allow water access from the flooded pump chamber 58 between the bearings 54, 56 and the stationary shaft 52 to provide lubrication for the bearings 54, 56. In some embodiments, the main bearing 54 and/or the secondary bearings 56 can be ceramic bearings. The ability to keep the rotor unit 40 centered and stable within the first cup 48, as described above, removes the need for additional components to track rotor displacement and to apply counteracting forces, for example through electromagnets, in order to keep the rotor unit 40 centered.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:
1. A pump assembly comprising:
a pump chamber including an inlet and an outlet;
a first cup at least partially enclosing the pump chamber and including a protrusion with a central recess;
a shaft positioned within the central recess;
a substantially hemispherical rotor unit including a plurality of ferrous metal elements spaced apart from each other and molded in plastic, the rotor unit positioned inside the first cup and rotatable around the shaft, wherein the plastic of the rotor unit has an outer surface that is curved in two perpendicular axes, wherein the plastic of the rotor unit defines a central cutout through the rotor unit, wherein the curved outer surface of the plastic is curved between two radial points having differing lengths extending from a center of the rotor unit to the curved outer surface of the plastic, wherein the plurality of ferrous metal elements are disposed on the outer surface of the plastic of the rotor unit, wherein each of the ferrous metal elements include a first surface disposed on the outer surface of the plastic of the rotor unit and a second surface opposite the first surface, and wherein the first surface and the second surface of each of the plurality of ferrous metal elements are curved around both of the two perpendicular axes;
an impeller coupled to the rotor unit; and
a stator unit positioned outside of the first cup and separated from the first cup by a second cup, wherein the stator unit includes a stator cup and a ring magnet, wherein the curved outer surface of the plastic of the rotor unit is disposed facing the ring magnet of the stator unit, wherein the plastic of the rotor unit is positioned to leave the second surface of the plurality of ferrous metal elements physically exposed to an inner surface of the first cup, and wherein the second cup includes a protrusion with a central recess that is configured to align with the protrusion with the central recess of the first cup.
2. The pump assembly of claim 1, wherein the first cup includes a curved inner surface and wherein the curved outer surface of the plastic minimizes a gap between the first cup and the rotor unit.
3. The pump assembly of claim 1, wherein the plurality of ferrous metal elements are constructed of stainless steel.
4. The pump assembly of claim 1, wherein the plurality of ferrous metal elements include four ferrous metal elements.

5. The pump assembly of claim 1, wherein the ring magnet has a curved inner surface.

6. The pump assembly of claim 1, wherein the shaft keeps the rotor unit substantially centered within the first cup.

7. The pump assembly of claim 1, wherein the rotor unit and the impeller are coupled together by fitting protrusions of the impeller into receiving holes of an upper surface of the rotor unit.

8. The pump assembly of claim 1, wherein the central cutout includes an annular shoulder, and the annular shoulder contacts the protrusion of the first cup when the rotor unit tilts within the first cup.

9. The pump assembly of claim 1, wherein the rotor unit includes a lip, and wherein the plurality of ferrous metal elements are disposed flush with the lip of the rotor unit.

10. The pump assembly of claim 1, wherein the rotor unit includes a first flat surface and a second flat surface, wherein the curved outer surface of the plastic meets the first flat surface and the second flat surface.

11. A pump assembly comprising:
a disposable portion including:
a first cup including a protrusion with a central recess,
a shaft positioned within the central recess,
a substantially hemispherical rotor unit including a plurality of ferrous metal elements spaced apart from each other and molded in plastic, the rotor unit positioned inside the first cup and rotatable around the shaft, wherein the plastic of the rotor unit has an outer surface that is curved in two perpendicular axes, wherein the plastic of the rotor unit defines a central cutout through the rotor unit, wherein the curved outer surface of the plastic is curved between two radial points having differing lengths extending from a center of the rotor unit to the curved outer surface of the plastic, wherein the plurality of ferrous metal elements are disposed on the outer surface of the plastic of the rotor unit, wherein each of the ferrous metal elements include a first surface disposed on the outer surface of the plastic of the rotor unit and a second surface opposite the first surface, wherein the first surface and the second surface of each of the plurality of ferrous metal elements are curved around both of the two perpendicular axes, and wherein the plastic of the rotor unit is positioned to leave the second surface of the plurality of ferrous metal elements physically exposed to an inner surface of the first cup, and
an impeller coupled to the rotor unit; and
a reusable portion including:
a stator unit with a stator cup and a ring magnet, wherein the curved outer surface of the plastic of the rotor unit is disposed facing the ring magnet of the stator unit;
a second cup positioned over the stator unit and the ring magnet so that the second cup physically separates the first cup from the stator unit when the disposable portion and the reusable portion are coupled together, wherein the second cup includes a protrusion with a central recess that is configured to align with the protrusion with the central recess of the first cup;
the disposable portion and the reusable portion being removably coupled together by positioning the first cup within the stator cup so that the ring magnet encircles the rotor unit.

12. The pump assembly of claim 11, wherein the ring magnet includes a curved inner surface.

13. The pump assembly of claim 11, wherein the reusable portion includes a motor coupled to the stator unit.

14. The pump assembly of claim 11, wherein the plurality of ferrous metal elements have an outer curvature that matches the curved outer surface of the plastic.

15. The pump assembly of claim 11, wherein the rotor unit is a substantially solid piece with the central cutout.

* * * * *